United States Patent
Cheng et al.

(10) Patent No.: US 10,072,285 B2
(45) Date of Patent: Sep. 11, 2018

(54) RNA AMPLIFICATION METHODS (71) Applicant: Bio-Rad Laboratories, Inc., Hercules, CA (US)

(72) Inventors: Man Cheng, Danville, CA (US); Xiao-Song Gong, Richmond, CA (US); Yan Wang, San Francisco, CA (US); Adam M. McCoy, Davis, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 335 days.

(21) Appl. No.: 14/828,242

(22) Filed: Aug. 17, 2015

(65) Prior Publication Data

US 2016/0053305 A1    Feb. 25, 2016

Related U.S. Application Data (60) Provisional application No. 62/039,094, filed on Aug. 19, 2014.

(51) Int. Cl.
| | | |
|---|---|---|
| *C12Q 1/68* | (2018.01) | |
| *C12Q 1/6806* | (2018.01) | |
| *C12P 19/34* | (2006.01) | |
| *C12Q 1/686* | (2018.01) | |

(52) U.S. Cl.
CPC .......... *C12Q 1/6806* (2013.01); *C12P 19/34* (2013.01); *C12Q 1/686* (2013.01)

(58) Field of Classification Search
None
See application file for complete search history.

(56) References Cited

U.S. PATENT DOCUMENTS

| | | | |
|---|---|---|---|
| 8,415,129 B2 | 4/2013 | Wang | |
| 8,476,045 B2 | 7/2013 | Wang et al. | |
| 2007/0077582 A1 | 4/2007 | Slepnev et al. | |
| 2010/0279305 A1* | 11/2010 | Kuersten | C12Q 1/6855 435/6.16 |
| 2013/0184175 A1 | 7/2013 | Beaudenon-Huibregtse et al. | |
| 2013/0203122 A1 | 8/2013 | Gong et al. | |
| 2013/0231261 A1 | 9/2013 | Ozinsky et al. | |

FOREIGN PATENT DOCUMENTS

| | | | | |
|---|---|---|---|---|
| WO | 2007/035684 A2 | 3/2007 | | |
| WO | WO-2007035684 A2 * | 3/2007 | .......... | C12Q 1/6851 |
| WO | 2008097957 A2 | 8/2008 | | |
| WO | 2010/120803 A2 | 10/2010 | | |
| WO | WO-2010120803 A2 * | 10/2010 | ............. | C12Q 1/682 |
| WO | 2012/116146 A1 | 8/2012 | | |

OTHER PUBLICATIONS

Hunt, "The Next Generation", The RNA Underworld, Available online at https://aghunt.wordpress.com/2011/02/28/the-next-generation/, Feb. 28, 2011, 8 pages.

Supplementary Partial European Search Report dated Jul. 24, 2017 in EP Appln. No. 15833024.1; 15 pages.

* cited by examiner

*Primary Examiner* — Suryaprabha Chunduru (74) *Attorney, Agent, or Firm* — Kilpatrick Townsend & Stockton LLP (57) ABSTRACT

Methods of detecting and amplifying short RNAs are provided.

7 Claims, 6 Drawing Sheets

Specification includes a Sequence Listing.

RNA AMPLIFICATION METHODS

CROSS-REFERENCE TO RELATED PATENT APPLICATIONS

The present application claims benefit of priority to U.S. Provisional Patent Application No. 62/039,094, filed Aug. 19, 2014, which is incorporated by reference for all purposes.

BACKGROUND OF THE INVENTION

A number of types of non-coding short RNAs occur in cells. Examples of such RNAs include but are not limited to miRNA, snoRNA, piRNA, or lncRNA.

BRIEF SUMMARY OF THE INVENTION

Methods of amplifying a short RNA molecule are provided. In some embodiments, the methods comprise: obtaining an RNA sample comprising a short RNA target molecule; contacting the sample comprising the short RNA target molecule and at least one RNA-comprising template molecule with a reverse transcriptase, wherein the short RNA target molecule anneals to the RNA-comprising template molecule and the reverse transcriptase reverse transcribes the RNA-comprising template molecule by extending the annealed short RNA molecule to form a duplex comprising a short RNA target molecule/cDNA hybrid polynucleotide annealing to the template RNA molecule; contacting the duplex with RNase H activity, thereby excising ribonucleotides in a portion of the RNA-comprising template molecule in the duplex that anneals to deoxyribonucleotides in the short RNA target molecule/cDNA hybrid polynucleotide; reverse transcribing at least the short RNA target molecule portion of the short RNA target molecule/cDNA hybrid polynucleotide by extending a first oligonucleotide primer that anneals to the single-stranded short RNA target molecule/cDNA hybrid with the reverse transcriptase to form a DNA molecule comprising a sequence complementary to the short RNA target molecule; and amplifying the DNA molecule comprising a sequence complementary to the short RNA target molecule with a DNA polymerase, thereby amplifying the short RNA sequence.

In some embodiments, the first oligonucleotide primer is added from an exogenous source.

In some embodiments, the short RNA is a miRNA, snoRNA, piRNA, or lncRNA.

In some embodiments, short RNA is 30 or fewer nucleotides in length

In some embodiments, the RNA-comprising template molecule is a naturally-occurring RNA molecule from the sample. In some embodiments, the first oligonucleotide primer has 12-16 nucleotides and comprises a 5' portion not complementary to the single-stranded short RNA target molecule/cDNA hybrid polynucleotide and a 3' portion that is complementary to the single-stranded short RNA target molecule/cDNA hybrid polynucleotide. In some embodiments, the first oligonucleotide primer comprises at least 6 nucleotides long that are complementary to the single-stranded short RNA target molecule/cDNA fusion polynucleotide. In some embodiments, the 3' portion of the first oligonucleotide primer is 6-10 nucleotides long. In some embodiments, the 5' portion of the first oligonucleotide primer is 3-6 nucleotides long.

In some embodiments, the DNA polymerase has a DNA footprint of 6-10 nucleotides. In some embodiments, the DNA polymerase is linked to a DNA-binding domain having a DNA foot print of 4-6 nucleotides.

In some embodiments, the RNA-comprising template molecule is heterologous to the sample. In some embodiments, the RNA-comprising template molecule comprises (i) a 3' portion complementary to the short RNA target and composed of RNA and (ii) a 5' portion that forms a 5' overhang when the RNA-comprising template molecule is annealed to the short RNA target molecule. In some embodiments, the 5' portion is DNA except for a 1-2 ribonucleotide portion of the 5' portion linked to the '3 portion. In some embodiments, the first primer is the 5' DNA portion that is released by the RNaseH activity. In some embodiments, the 3' portion and 5' portion are RNA. In some embodiments, the contacting of the sample comprises contacting the sample with the short RNA target and a plurality of RNA-comprising template molecules having a 5' portion and a 3' portion, wherein said 3' portion comprises a degenerate sequence of at least 4 nucleotides such that the plurality comprises a variety of RNA-comprising molecules having different 3 portions and identical 5 portions.

In some embodiments, a RNaseH enzyme is added to the duplex, thereby contacting the duplex with RNaseH activity.

In some embodiments, a RNaseH enzyme is from the reverse transcriptase.

In some embodiments, the amplifying comprises generating an amplicon, and the method further comprises nucleotide sequencing the amplicon.

In some embodiments, the method further comprises quantifying the amount of short RNA target molecule in the sample.

Also provided are methods of amplifying a non-polyA tailed RNA less than 30 nucleotides long. In some embodiments, the methods comprise: reverse transcribing the RNA by extending a first primer having at least 6 contiguous nucleotides complementary to the RNA, to produce a first strand cDNA comprising a sequence at least 10 nucleotides long, in addition to the primer sequence, that is complementary to the RNA, amplifying the first strand cDNA with a DNA polymerase-DNA binding domain fusion to extend a second primer, wherein the DNA polymerase has a foot print of 6-10 base pairs and the DNA binding domain has a footprint of 3-5 base pairs and wherein the second primer comprises contiguous base pairs complementary to a 3' region of the first strand cDNA to produce a double-stranded cDNA.

In some embodiments, the first primer comprises a 5' portion not complementary to the RNA.

In some embodiments, the second primer comprises 12-16 contiguous base pairs complementary to a 3' region of the first strand cDNA In some embodiments, the polymerase is a Taq Stoffel fragment or an analog thereof.

In some embodiments, the DNA binding domain is an Sso7d DNA binding domain.

In some embodiments, the RNA is a miRNA, snoRNA, piRNA, or lncRNA.

In some embodiments, the first primer has 6-12 contiguous nucleotides complementary to the RNA.

In some embodiments, the 5' portion is 3-6 nucleotides long.

In some embodiments, the amplifying comprises generating an amplicon, and the method further comprises nucleotide sequencing the amplicon. In some embodiments, the method further comprises quantifying the amount of the non-polyA tailed RNA in the sample.

Also provided are methods of generating cDNA from non-polyA tailed RNA. In some embodiments, the method comprises: adding random poly-W (A/T) or poly-S(G/C) nucleotide sequences to the 3' end of target non-polyA tailed RNA with a terminal transferase to form RNA molecules comprising degenerate nucleotide sequences at the 3' end of the molecules; submitting the RNA molecules comprising the random poly-W or poly-S nucleotide sequences to conditions such that the RNA molecules comprising the random poly-W or poly-S nucleotide sequences anneal to form a duplex of a first and second RNA molecule annealed to each other via the random poly-W or poly-S nucleotide sequences; and extending the 3' ends of the molecules in the duplex with a DNA polymerase to form (i) a first cDNA complementary to the first RNA molecule of the duplex and (ii) a second cDNA complementary to the second RNA molecule of the duplex, wherein the first and second cDNAs further comprise a 5' sequence that is a complement of the random poly-W or poly-S nucleotide sequence.

In some embodiments, the RNA is a miRNA, snoRNA, piRNA, or lncRNA.

In some embodiments, the method further comprises digesting the RNA molecules with an RNAse H activity.

In some embodiments, the method further comprises amplifying the first or second cDNA with a primer that anneals to the complement of the degenerate sequence.

In some embodiments, the adding further comprises contacting the non-polyA tailed RNA with a poly A polymerase (e.g. a yeast poly A polymerase).

In some embodiments, the amplifying comprises generating an amplicon, and the method further comprises nucleotide sequencing the amplicon.

In some embodiments, the method further comprises quantifying the amount of the non-tailed RNA in the sample.

Additional aspects of the inventions are found elsewhere herein.

BRIEF DESCRIPTION OF THE DRAWINGS

FIGS. 5 A and B illustrate steps of a method for reverse transcribing and then amplifying a short (e.g., 20-25 nucleotide long) polynucleotide sequence using a tailed reverse transcription (RT) primer. The amplification can be achieved, for example, using a polymerase having a small nucleotide footprint linked to a DNA binding domain protein having a small nucleotide footprint.

DEFINITIONS

The term "polymerase" refers to an enzyme that performs template-directed synthesis of polynucleotides. The term encompasses both a full length polypeptide and a domain that has polymerase activity. DNA polymerases are well-known to those skilled in the art, and include but are not limited to DNA polymerases isolated or derived from *Pyrococcus furiosus, Thermococcus litoralis*, and *Thermotoga maritime*, or modified versions thereof. They include both DNA-dependent polymerases and RNA-dependent polymerases such as reverse transcriptase. At least five families of DNA-dependent DNA polymerases are known, although most fall into families A, B and C. There is little or no sequence similarity among the various families. Most family A polymerases are single chain proteins that can contain multiple enzymatic functions including polymerase, 3' to 5' exonuclease activity and 5' to 3' exonuclease activity. Family B polymerases typically have a single catalytic domain with polymerase and 3' to 5' exonuclease activity, as well as accessory factors. Family C polymerases are typically multi-subunit proteins with polymerizing and 3' to 5' exonuclease activity. In *E. coli*, three types of DNA polymerases have been found, DNA polymerases I (family A), II (family B), and III (family C). In eukaryotic cells, three different family B polymerases, DNA polymerases α, δ, and ε, are implicated in nuclear replication, and a family A polymerase, polymerase γ, is used for mitochondrial DNA replication. Other types of DNA polymerases include phage polymerases. Similarly, RNA polymerases typically include eukaryotic RNA polymerases I, II, and III, and bacterial RNA polymerases as well as phage and viral polymerases. RNA polymerases can be DNA-dependent and RNA-dependent.

"Thermally stable polymerase," as used herein, refers to any enzyme that catalyzes polynucleotide synthesis by addition of nucleotide units to a nucleotide chain using DNA or RNA as a template and has an optimal activity at a temperature above 45° C.

The term "Sso7-like protein" or "Sso7," as used herein, refers to polypeptide variants, alleles, mutants, and interspecies homologs that: (1) have an amino acid sequence that has greater than about 60% amino acid sequence identity, 65%, 70%, 75%, 80%, 85%, 90%, 91%, 92%, 93%, 94%, 95%, 96%, 97%, 98% or 99% or greater amino acid sequence identity to SEQ ID NO:4 or 10 of PCT Publication No. WO 2012/177695. The term includes both full-length Sso7 polypeptides and fragments of the polypeptides that have sequence non-specific double-stranded binding activity. Sso7-like proteins include Sac7d, Sac7e, Ssh7b, and Sto7e. Exemplary mutants of Sso7d include those described in PCT Publication No. WO 2012/138417.

A "domain" refers to a unit of a protein or protein complex, comprising a polypeptide subsequence, a complete polypeptide sequence, or a plurality of polypeptide sequences where that unit has a defined function. The function is understood to be broadly defined and can be ligand binding, catalytic activity, or can have a stabilizing effect on the structure of the protein.

The term "DNA binding domain" refers to a protein domain that binds DNA in a sequence non-specific manner. In some embodiments, the DNA binding domain is a protein domain which binds with significant affinity to DNA, for which there is no known nucleic acid which binds to the protein domain with more than 100-fold more affinity than another nucleic acid with the same nucleotide composition but a different nucleotide sequence.

The terms "join" or "link" refer to any method known in the art for functionally connecting protein domains, including without limitation recombinant fusion with or without intervening domains, intein-mediated fusion, non-covalent association, and covalent bonding, including disulfide bonding; hydrogen bonding; electrostatic bonding; and conformational bonding, e.g., antibody-antigen, and biotin-avidin associations.

The term "nucleic acid amplification" or "amplification reaction" refers to any in vitro means for multiplying the copies of a target sequence of nucleic acid. Such methods include but are not limited to polymerase chain reaction (PCR), DNA ligase chain reaction (see U.S. Pat. Nos. 4,683,195 and 4,683,202; PCR Protocols: A Guide to Methods and Applications (Innis et al., eds, 1990)), (LCR), QBeta RNA replicase, and RNA transcription-based (such as TAS and 3SR) amplification reactions as well as others known to those of skill in the art.

"Amplifying" refers to a step of submitting a solution to conditions sufficient to allow for amplification of a polynucleotide. Components of an amplification reaction include, e.g., primers, a polynucleotide template, polymerase, nucleotides, and the like. The term amplifying typically refers to an "exponential" increase in target nucleic acid. However, amplifying as used herein can also refer to linear increases in the numbers of a select target sequence of nucleic acid, such as is obtained with cycle sequencing.

"Polymerase chain reaction" or "PCR" refers to a method whereby a specific segment or subsequence of a target double-stranded DNA, is amplified in a geometric progression. PCR is well known to those of skill in the art; see, e.g., U.S. Pat. Nos. 4,683,195 and 4,683,202; and PCR Protocols: A Guide to Methods and Applications, Innis et al., eds, 1990. Exemplary PCR reaction conditions typically comprise either two or three step cycles. Two step cycles have a denaturation step followed by a hybridization/elongation step. Three step cycles comprise a denaturation step followed by a hybridization step followed by a separate elongation step. PCR can be performed as end-point PCR (i.e., only monitored at an end point) or as quantitative PCR (monitored in "real time").

An "olignucleotide primer" or "primer" refers to an oligonucleotide sequence that anneals to a sequence on a target nucleic acid and serves as a point of initiation of nucleic acid synthesis. Primers can be of a variety of lengths and are often less than 50 nucleotides in length, for example 12-30 nucleotides in length. The length and sequences of primers for use in PCR can be designed based on principles known to those of skill in the art; see, e.g., Innis et al., supra.

The terms "nucleic acid" and "polynucleotide" are used interchangeably herein to refer to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, and peptide nucleic acids (PNAs).

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The terms "identical" or percent "identity," in the context of two or more nucleic acids or polypeptide sequences, refer to two or more sequences or subsequences that are the same. Sequences are "substantially identical" to each other if they have a specified percentage of nucleotides or amino acid residues that are the same (e.g., at least 60%, 65%, 70%, 75%, 80%, 85%, 90%, 91%, 92%, 93%, 94%, 95%, 96%, 97%, 98%, or 99% identity) over a specified region where indicated, or across the entire reference sequence if not otherwise indicated, when compared and aligned for maximum correspondence over a comparison window, or designated region as measured using one of the following sequence comparison algorithms or by manual alignment and visual inspection. These definitions also refer to the complement of a test sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are commonly used, or alternative parameters can be designated. The sequence comparison algorithm then calculates the percent sequence identities or similarities for the test sequences relative to the reference sequence, based on the program parameters.

A "comparison window," as used herein, includes reference to a segment of contiguous positions, for example from 20 to 600 contiguous positions, about 50 to about 200, or about 100 to about 150, in which a sequence may be compared to a reference sequence of the same number of contiguous positions after the two sequences are optimally aligned. Methods of alignment of sequences for comparison are well known in the art. Optimal alignment of sequences for comparison can be conducted, for example, by the local homology algorithm of Smith and Waterman (*Adv. Appl. Math.* 2:482, 1970), by the homology alignment algorithm of Needleman and Wunsch (*J. Mol. Biol.* 48:443, 1970), by the search for similarity method of Pearson and Lipman (*Proc. Natl. Acad. Sci. USA* 85:2444, 1988), by computerized implementations of these algorithms (e.g., GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

Algorithms suitable for determining percent sequence identity and sequence similarity are the BLAST and BLAST 2.0 algorithms, which are described in Altschul et al. (*Nuc. Acids Res.* 25:3389-402, 1977), and Altschul et al. (*J. Mol. Biol.* 215:403-10, 1990), respectively. Software for performing BLAST analyses is publicly available through the National Center for Biotechnology Information (on the world wide web at ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a word length (W) of 11, the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

DETAILED DESCRIPTION OF THE INVENTION

I. Introduction

While short RNAs are of great interest in a large number of biological contexts, amplification and detection of short RNAs can be difficult. Presented herein are several methods for amplification and detection of short RNAs from a sample.

In some embodiments, the methods do not employ an initial primer extension step in which a primer is extended to form a cDNA using the target short RNA as a template. Instead, in some embodiments, the method involves using the target short RNA itself as a primer to perform primer extension on a different template polynucleotide. As discussed in more detail below, the template polynucleotide can be a second RNA endogenously present in the sample, or can be an exogenous RNA-containing oligonucleotide (e.g., i.e., from the sample).

Other methods described herein allow for primer extension using the short RNA as a template. In some of these embodiments, a polymerase with a small nucleotide footprint fused to a DNA binding-protein with a small nucleotide footprint is used for primer extension. In some embodiments, the primer has (1) a 3' portion complementary to the 3' portion of the target short RNA and (2) a 5' portion that forms an overhang (i.e., it is not complementary, and does not anneal, to the target short RNA). Use of the small footprint polymerase with the DNA binding domain allows for extension of the target short RNA in circumstances where a polymerase such as Taq polymerase would be inefficient or would not be able to extend the primer. Because the initial primer has a 5' overhang, the resulting cDNA will be longer than the target short RNA (e.g., by the number of nucleotides in the 5' overhang of the primer). The resulting cDNA can then be amplified using a "forward" primer that anneals (e.g., is complementary) to the '3 portion of the cDNA in combination with the primer with the 5' overhang, which functions as a "reverse" primer.

Exemplary target RNAs that can be detected and amplified using the methods described herein include, but are not limited to, miRNA, snRNA, snoRNA, piRNA, or lncRNA. MicroRNAs (miRNAs), typically 18 to 25 nt in length, are non-protein-coding RNAs that can inhibit the translation of target mRNAs (see, e.g., Croce and Calin, *Cell* 122(1): 6-7 (2005)). Other small RNAs include small nucleoplasmic RNAs (snRNAs) and small nucleolar RNAs (snoRNAs). These small RNA molecules can function, for example, in mRNA splicing (U1, U2, and U4 to U6 snRNAs), mRNA and rRNA processing (U7 snRNA; U3 and U8 snoRNAs), and site selection for RNA modification by methylation of the 2' hydroxyl group (box C/D snoRNAs) or by pseudouridine formation (box H/ACA snoRNAs). Piwi-interacting RNAs (piRNAs) were identified through association with Piwi proteins in mammalian. piRNAs can range from 26-30 nucleotides in length. Long noncoding RNA (lncRNA) have also been described.

II. Method

As briefly summarized above, in some embodiments, the methods do not require or involve reverse transcription of the target RNA until after the target RNA has itself acted as a primer. In some embodiments, another RNA-containing polynucleotide can be used as a template for reverse transcription, with the target RNA functioning as a primer. In these embodiments, the target RNA will be linked to the resulting cDNA. The resulting polynucleotide will therefore be partially composed of RNA nucleotides (i.e., the target RNA sequence) and partially composed of DNA (i.e., the nucleotides added in the reverse transcription).

Figure 1:
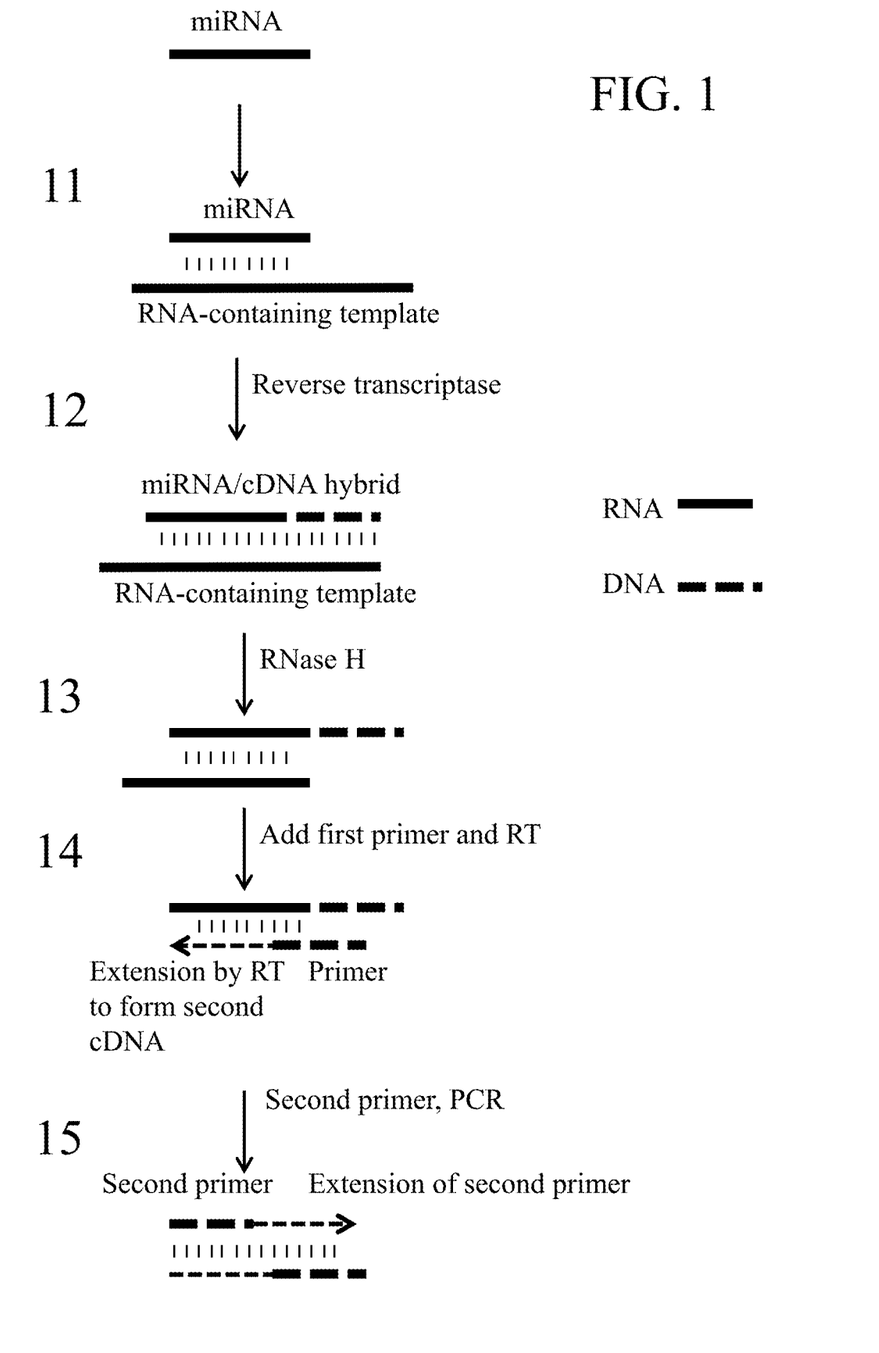
FIG. 1 illustrates steps of a method for using an RNA-containing template to detect a target short RNA. While the figure refers to the target RNA as an "miRNA", it will be appreciated that other types of RNA can also be detected.

FIG. 1 exemplifies an embodiment as described above. In FIG. 1, step 11, a target miRNA is exposed to conditions to anneal the target miRNA to an RNA-containing template forming a target/template duplex. The RNA-containing template can be, for example, an mRNA or other longer RNA from the same or a different biological sample from which the target RNA (e.g., miRNA) was obtained. Other different RNA-containing template options are described below.

As exemplified in FIG. 1, step 12, the annealed target/template complex can be exposed to a protein having reverse transcriptase activity such that the reverse transcriptase activity extends the 3' end of the target RNA to generate a cDNA complementary to at least a portion of the template RNA. Any conditions for reverse transcription reactions can be used. The resulting cDNA will be composed of a 5' portion made of the target RNA, and a 3' portion made up of the cDNA. The resulting target RNA/cDNA hybrid polynucleotide can be of any length that incorporates the target RNA length and at least some deoxynucleotides complementary to the template RNA. The length of the cDNA portion of the RNA target/cDNA hybrid polynucleotide will depend on the length of the template RNA as well as the position at which the target RNA anneals to the template RNA. In some embodiments, the cDNA will be at least 10, 20, 30, 40, 50, 100, or 150 nucleotides, e.g., 10-100 or 50-500 nucleotides.

Any of a variety of reverse transcriptases can be used. Exemplary reverse transcriptases include but are not limited to murine leukemia virus (MLV) reverse transcriptase, Avian Myeloblastosis Virus (AMV) reverse transcriptase, Respiratory Syncytial Virus (RSV) reverse transcriptase, Equine Infectious Anemia Virus (EIAV) reverse transcriptase, Rous-associated Virus-2 (RAV2) reverse transcriptase, SUPER-SCRIPT II reverse transcriptase, SUPERSCRIPT I reverse transcriptase, THERMOSCRIPT reverse transcriptase and MMLV RNase H⁻ reverse transcriptases. In additional embodiments, a DNA polymerase that functions as an RNA polymerase can be used. For example, Tth and Z05, which are DNA polymerases, can function as reverse transcriptase in the presence of manganese. The concentration of the reverse transcriptase can vary and optimal concentrations can be determined empirically and depend on the particular reverse transcriptase used.

The portion the template RNA complementary to the newly-formed cDNA can subsequently be cleaved from the remainder of the RNA-containing template polynucleotide. In some embodiments, RNase H is used for this purpose. RNase H (Ribonuclease H) is an endoribonuclease that specifically hydrolyzes the phosphodiester bonds of RNA which is annealed to DNA. RNase H does not digest single or double-stranded DNA. Following formation of the cDNA, RNAse H can be applied to the RNA template/cDNA double-stranded complex. Because of RNase H's particular activity, only RNA nucleotides annealing to deoxynucleotides of the cDNA will be removed from the RNA template. Alternatively, in some embodiments, the reverse transcriptase used will have inherent RNaseH activity that will cleave and degrade the RNA as described above. This aspect is exemplified, for example, in steps 13, 23, and 33 of FIGS. 1-3, respectively.

Following the above-described steps, a primer (referred to for convenience as "first primer") complementary to the cDNA portion of the target RNA/cDNA hybrid can be annealed to the cDNA and a second reverse transcription reaction can be performed. In this second reverse transcription reaction (exemplified in steps 14, 24, and 34 of FIGS. 1-3, respectively), a first primer that anneals to the cDNA is extended to form a second cDNA complementary to the target RNA. As discussed more below, the first primer can anneal to the cDNA sequence or can anneal to both the target RNA and the cDNA, annealing to the junction between the two sequences. The first primer can be added exogenously, or as discussed below, can be generated in some circumstances by the RNaseH activity. The resulting second cDNA therefore comprises a sequence complementary to the entire, or substantially the entire, target RNA and further comprises the first primer sequence. The second cDNA can subsequently be amplified as desired using standard techniques. This is exemplified in steps 15, 25, and 35 of FIGS. 1-3, respectively. For example, in some embodiments, the polymerase chain reaction is used to amplify the second cDNA. For example in some embodiments a "reverse" primer complementary to the 3' portion of the second cDNA can be used in combination with the first primer and a thermostable polymerase under thermocyclic conditions to generate a double stranded DNA comprising the target RNA sequence. If desired, the PCR can be performed quantitatively and be monitored in real-time.

Figure 2:
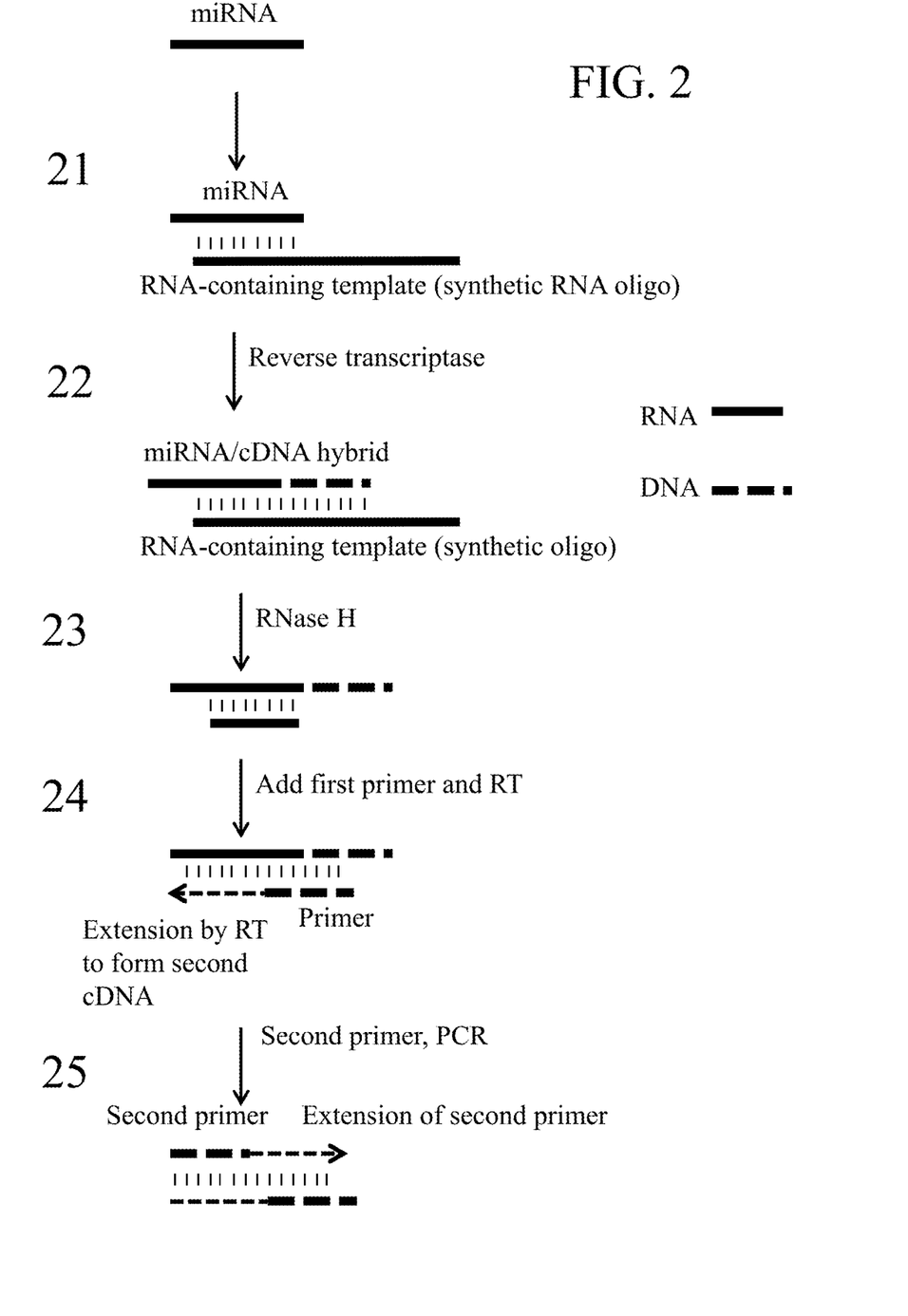
FIG. 2 illustrates steps of a method for using an RNA-containing template that is a synthetic RNA oligonucleotide to detect a target short RNA. While the figure refers to the target RNA as an "miRNA", it will be appreciated that other types of RNA can also be detected.
Figure 3:
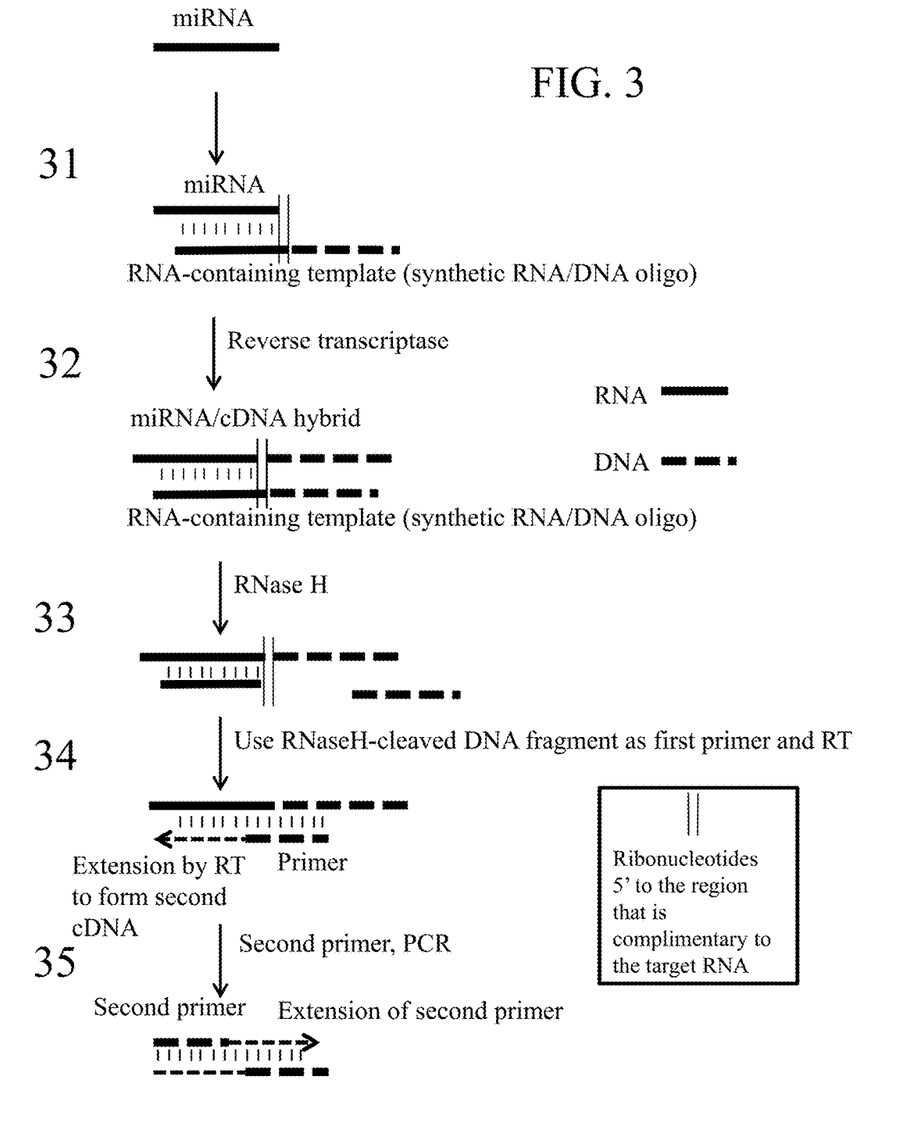
FIG. 3 illustrates steps of a method for using an RNA-containing template that is an RNA/DNA oligonucleotide to detect a target short RNA. While the figure refers to the target RNA as an "miRNA", it will be appreciated that other types of RNA can also be detected.

As discussed above, the method can employ an RNA-containing template polynucleotide. The embodiment illustrated in FIG. 1 is a naturally-occurring RNA from a biological sample. In alternative embodiments, the RNA-containing template polynucleotide can be a synthetic polynucleotide. For example, as shown in FIG. 2, the RNA-containing template is a synthetic RNA oligonucleotide. In another alternative, the synthetic RNA-containing template is partially DNA and partially RNA (exemplified in FIG. 3). In these embodiments, the 5' end portion of the template is DNA and the 3' end portion of the template is RNA. As shown in FIG. 3, the RNaseH activity in this latter option releases the DNA portion of the template, which can then be available to function as the first primer in the second reverse transcription step, without addition of an exogenous first primer.

The 3' end portion of the template will be complementary to the target RNA, or at least substantially complementary such that the 3' end portion of the template anneals to the target RNA under conditions in which the reverse transcriptase is active and can extend the target RNA using the RNA-containing template polynucleotide as a template. The 5' portion is not complementary to the target RNA and acts as a non-annealing tail. The 3' end portion of the template will be of sufficient length to allow annealing to the target RNA and can be, for example, at least 4, 5, 6, 7, 8, 9, 10, or more nucleotides long, e.g., 5-30 or more nucleotides. Of course, the annealing sequence of the template will be no longer than the target RNA itself. The portion of the template composed of RNA will extend at least one (e.g., 1, 2, 3, or more) nucleotide beyond the annealing portion of the template (said another way, the 5' non-annealing portion of the template is DNA except for a short (e.g., 1, 2, 3, or more nucleotides) that is composed of ribonucleotides). This is exemplified in FIG. 3 bounded by vertical lines. The effect of these particular nucleotides being RNA is that the complementary nucleotides in the resulting cDNA formed in the reverse transcription step will be DNA, thereby forming for these particular nucleotides an RNA/DNA duplex, which enables cleavage by the RNase H activity. While not shown with vertical lines in FIGS. 1-2, this same feature occurs in these embodiments because the entire template is composed of RNA and thus forms an RNA/DNA duplex that can be degraded by RNase H. As explained above, RNase H excises RNA in RNA/DNA duplexes, and thus the presence of one or more RNA nucleotides just after the annealing sequence of the template will allow for a region of the RNA/DNA duplex that will subsequently be cleaved by RNase H activity. Degradation of at least a portion of, and ideally all of, the template allows for the first primer to subsequently anneal to the cDNA without (or with reduced) competition from the portion of the template complementary to the cDNA.

The 5' end portion of the template can vary in length but in some embodiments in which the template is composed of RNA and DNA, at least the first three nucleotides in the 5' end of the template will be DNA. In some embodiments, the 5' end portion is 4, 5, 6, 7, 8, or more DNA nucleotides, e.g., from 3-100 or more nucleotides.

In some embodiments, the synthetic RNA-containing template polynucleotide can be provided in the form of a plurality of RNA-containing template polynucleotides wherein some or all of the RNA sequence (i.e., at least the 3' end of the template) is a degenerate sequence. By providing a random sequence at the 3' end of the template, more than one short RNA target can be amplified. Thus, for example, a library of small RNAs can be generated.

Figure 4:
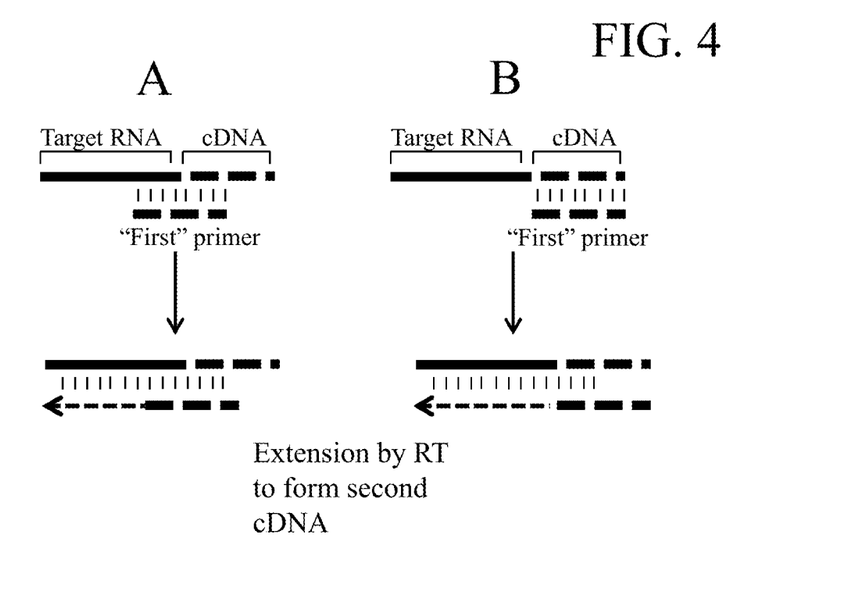
FIG. 4 illustrates some different possible embodiments for hybridization of the "first" primer to the target RNA/cDNA hybrid. As depicted in part A of the figure, portions of the first primer can anneal to 3' portions of the target RNA sequence and to 5' portions of the cDNA sequence. Alternatively, part B of the figure illustrates an embodiment in which the first primer anneals solely to the cDNA sequence. The embodiment in part B of the figure will find most use when a synthetic template is used because the synthetic template's sequence will be known. However, it will be appreciated that the part B embodiment can also be used in circumstances where an endogenous template RNA is used and the template RNA sequence is known.

As noted above, the method involves a second reverse transcription step to generate a second cDNA based on a primer ("first primer") complementary to the cDNA portion of the target RNA/cDNA hybrid polynucleotide followed by amplification using the first primer and a reverse primer. The second reverse transcription step is exemplified in steps 14, 24, and 34 of FIGS. 1-3, respectively. The first primer is at least partially complementary to the cDNA portion of the target RNA/cDNA hybrid polynucleotide such that the first primer anneals to the complementary sequence in the cDNA. In embodiments in which endogenous RNA from the sample functions as a template, the sequence of the cDNA portion is not necessarily known. Thus, in some embodiments, at least the 3' portion of the first primer can be designed to be complementary to a portion of the 3' end of the target RNA such that the second reverse transcription step results in extension of the first primer using the target RNA as a template. This aspect is exemplified in FIG. 4, option "A." For example, a 5' portion of the first primer can be complementary to the cDNA and a 3' portion of the first primer can be complementary to the target RNA, thereby annealing to the junction of the cDNA and the target RNA. In an alternative embodiment, the first primer can be complementary only to the cDNA portion. These embodiments are useful, for example, when a synthetic RNA-containing template is used, as the 3' sequence of the template will then be known and thus the first primer can be designed to be complementary. This latter aspect is exemplified in FIG. 4, option "B."

The amplification step (e.g., steps 15, 25, or 35 of FIGS. 1-3, respectively) can involve extension of the first primer and the reverse primer to form a double-stranded amplicon comprising the target RNA sequence (albeit in DNA rather than RNA). The amplification will typically involve primer extension with a DNA polymerase (including but not limited to the polymerase chain reaction (PCR)). DNA polymerases useful in the present invention can be any polymerase capable of replicating a DNA molecule. Exemplary DNA polymerases are thermostable polymerases, which are especially useful in PCR. Thermostable polymerases are isolated from a wide variety of thermophilic bacteria, such as *Thermus aquaticus* (Taq), *Thermus brockianus* (Tbr), *Thermus flavus* (Tfl), *Thermus ruber* (Tru), *Thermus thermophilus* (Tth), *Thermococcus litoralis* (Tli) and other species of the *Thermococcus* genus, *Thermoplasma acidophilum* (Tac), *Thermotoga neapolitana* (Tne), *Thermotoga maritima* (Tma), and other species of the *Thermotoga* genus, *Pyrococcus furiosus* (Pfu), *Pyrococcus woesei* (Pwo) and other species of the *Pyrococcus* genus, *Bacillus sterothermophilus* (Bst), *Sulfolobus acidocaldarius* (Sac) *Sulfolobus solfataricus* (Sso), *Pyrodictium occultum* (Poc), *Pyrodictium abyssi* (Pab), and *Methanobacterium thermoautotrophicum* (Mth), and mutants, variants or derivatives thereof.

In some embodiments, the polymerase enzyme is a hybrid polymerase comprising a polymerase domain and a DNA binding domain. Such hybrid polymerases are known to show an increased processivity. See e.g., U.S. Patent Application Publication Nos. 2006/005174; 2004/0219558; 2004/0214194; 2004/0191825; 2004/0081963; 2004/0002076; 2003/0162173; 2003/0148330; 2003/0138830 and U.S. Pat. Nos. 6,627,424 and 7,445,898, each of which is hereby incorporated by reference in its entirety for all purposes and in particular for all teachings related to polymerases, hybrid/chimeric polymerases, as well as all methods for making and using such polymerases. In one aspect, the hybrid polymerases lack 3'-5' exonuclease activity. In one embodiment, such hybrid polymerases comprise a double point mutation in the polymerase domain that provides this exonuclease deficiency. In a specific embodiment, hybrid polymerases can comprise the double point mutation D141A/E143A in the polymerase domain.

In some embodiments, the binding domain of hybrid polymerases is from a thermostable organism and provides enhanced primer annealing at higher temperatures, e.g., temperatures above 45° C. For example, Sso7d and Sac7d are small (about 7 kd MW), basic chromosomal proteins from the hyperthermophilic archaeabacteria *Sulfolobus solfataricus* and *S. acidocaldarius*, respectively (see, e.g., Choli et al., *Biochimica et Biophysica Acta* 950:193-203, 1988; Baumann et al., *Structural Biol.* 1:808-819, 1994; and Gao et al, *Nature Struc. Biol.* 5:782-786, 1998). These proteins bind DNA in a sequence-independent manner and when bound, increase the Tm of DNA by up to 40° C. under some conditions (McAfee et al., *Biochemistry* 34:10063-10077, 1995). These proteins and their homologs are often used as the sequence-non-specific DNA binding domain in improved polymerase fusion proteins. Sso7d, Sac7d, Sac7e and related sequences (referred to herein as "Sso7 sequences" or "Sso7 domains") are known in the art (see, e.g., accession numbers (P39476 (Sso7d); P13123 (Sac7d); and P13125 (Sac7e)). These sequences typically have at least 75% or greater, of 80%, 85%, 90%, or 95% or greater, amino acid sequence identity. For example, an Sso7 protein typically has at least 75% identity to an Sso7d sequence.

In further embodiments, hybrid polymerases of use are described for example in U.S. Patent Application Publication Nos. 2006/005174; 2004/0219558; 2004/0214194; 2004/0191825; 2004/0081963; 2004/0002076; 2003/0162173; 2003/0148330; 2003/0138830; PCT Publication No. WO 2012/138417; and U.S. Pat. Nos. 6,627,424 and 7,445,898, each of which is hereby incorporated by reference in its entirety for all purposes and in particular for all teachings related to polymerases, hybrid/chimeric polymerases, as well as all methods for making and using such polymerases. Examples of hybrid polymerase proteins and methods of generating hybrid proteins are also disclosed in WO2004011605, which is hereby incorporated by reference in its entirety for all purposes, and in particular for all teachings related to generating hybrid proteins.

In some embodiments, the DNA polymerase has a relatively small nucleotide footprint, and as a consequence, low binding affinity for a DNA substrate. Optimally, such polymerase is fused to a DNA binding protein also having a small footprint, wherein the fusion has an increased DNA affinity compared to the DNA polymerase alone. For example, in some embodiments, the DNA polymerase has a nucleotide footprint of 6-10 nucleotides and is linked to a sequence non-specific DNA binding protein having a nucleotide footprint of 3-6. The resulting fusion protein will have a small nucleotide footprint (e.g. 9-16 nucleotides) with increased binding affinity compared to the un-modified polymerase, allowing the fusion polymerase to efficiently extend a short primer in a template-specific manner when the template (and primer) is relatively short, e.g., when the template is too short to accommodate two regular sized primers (e.g. 18-20 nt long). For example, in some embodiments, the template has fewer than 40, 35, 30, 28, 26, 25, or 24 nucleotides. An exemplary DNA polymerase having a small nucleotide footprint is the Stoffel fragment of Taq polymerase or an analogous fragment from another thermostable (e.g., A family) polymerase. The Stoffel fragment is a Taq polymerase fragment lacking the amino-terminal 289 amino acids of Taq, and lacks 5'-3' exonuclease activity. A Stoffel fragment analog refers to a family A polymerase lacking an amino-terminal 5'-3' exonuclease domain. For example, in some embodiments, the analog has amino acids corresponding to those of the Stoffel fragment and lacks the N-terminal amino acids corresponding to the first 289 amino acids of Taq. For example, KlenTaq lacks the first 280 amino acids of Taq.

In some embodiments, original amount of a target RNA in a sample is determined following the amplification methods described herein. In some embodiments, quantitative amplification can be used to determine the original amount of a target RNA in a sample. Quantitative amplification methods (e.g., quantitative PCR or quantitative linear amplification) involve amplification of an nucleic acid template (e.g., a step corresponding to steps 15, 25, or 35 of FIGS. 1-3, respectively), directly or indirectly (e.g., determining a Ct value) determining the amount of amplified DNA, and then calculating the amount of initial template based on the number of cycles of the amplification. Amplification of a DNA locus using reactions is well known (see U.S. Pat. Nos. 4,683,195 and 4,683,202; PCR PROTOCOLS: A GUIDE TO METHODS AND APPLICATIONS (Innis et al., eds, 1990)). Typically, PCR is used to amplify DNA templates. However, alternative methods of amplification have been described and can also be employed, as long as the alternative methods amplify intact DNA to a greater extent than the methods amplify cleaved DNA. Methods of quantitative amplification are disclosed in, e.g., U.S. Pat. Nos. 6,180,349; 6,033,854; and 5,972,602, as well as in, e.g., Gibson et al., *Genome Research* 6:995-1001 (1996); DeGraves, et al., *Biotechniques* 34(1):106-10, 112-5 (2003); Deiman B, et al., *Mol Biotechnol.* 20(2):163-79 (2002). Amplifications can be monitored in "real time."

In some embodiments, quantitative amplification is based on the monitoring of the signal (e.g., fluorescence of a probe) representing copies of the template in cycles of an amplification (e.g., PCR) reaction. In the initial cycles of the PCR, a very low signal is observed because the quantity of the amplicon formed does not support a measurable signal output from the assay. After the initial cycles, as the amount of formed amplicon increases, the signal intensity increases to a measurable level and reaches a plateau in later cycles when the PCR enters into a non-logarithmic phase. Through a plot of the signal intensity versus the cycle number, the specific cycle at which a measurable signal is obtained from the PCR reaction can be deduced and used to back-calculate the quantity of the target before the start of the PCR. The number of the specific cycles that is determined by this method is typically referred to as the cycle threshold (Ct). Exemplary methods are described in, e.g., Heid et al. *Genome Methods* 6:986-94 (1996) with reference to hydrolysis probes.

One method for detection of amplification products is the 5'-3' exonuclease "hydrolysis" PCR assay (also referred to as the TaqMan™ assay) (U.S. Pat. Nos. 5,210,015 and 5,487,972; Holland et al., *PNAS USA* 88: 7276-7280 (1991); Lee et al., *Nucleic Acids Res.* 21: 3761-3766 (1993)). This assay detects the accumulation of a specific PCR product by hybridization and cleavage of a doubly labeled fluorogenic probe (the "TaqMan™ probe") during the amplification reaction. The fluorogenic probe consists of an oligonucleotide labeled with both a fluorescent reporter dye and a quencher dye. During PCR, this probe is cleaved by the 5'-exonuclease activity of DNA polymerase if, and only if, it anneals to the segment being amplified. Cleavage of the probe generates an increase in the fluorescence intensity of the reporter dye.

Another method of detecting amplification products that relies on the use of energy transfer is the "beacon probe" method described by Tyagi and Kramer, *Nature Biotech.* 14:303-309 (1996), which is also the subject of U.S. Pat. Nos. 5,119,801 and 5,312,728. This method employs oligonucleotide hybridization probes that can form hairpin structures. On one end of the hybridization probe (either the 5' or 3' end), there is a donor fluorophore, and on the other end, an acceptor moiety. In the case of the Tyagi and Kramer method, this acceptor moiety is a quencher, that is, the acceptor absorbs energy released by the donor, but then does not itself fluoresce. Thus, when the beacon is in the open conformation, the fluorescence of the donor fluorophore is detectable, whereas when the beacon is in hairpin (closed) conformation, the fluorescence of the donor fluorophore is quenched. When employed in PCR, the molecular beacon probe, which anneals to one of the strands of the PCR product, is in the open conformation and fluorescence is detected, while those that remain unhybridized will not fluoresce (Tyagi and Kramer, *Nature Biotechnol.* 14: 303-306 (1996)). As a result, the amount of fluorescence will increase as the amount of PCR product increases, and thus may be used as a measure of the progress of the PCR. Those of skill in the art will recognize that other methods of quantitative amplification are also available.

Various other techniques for performing quantitative amplification of a nucleic acids are also known. For example, some methodologies employ one or more probe oligonucleotides that are structured such that a change in fluorescence is generated when the oligonucleotide(s) is annealed to a target nucleic acid. For example, one such method involves is a dual fluorophore approach that exploits fluorescence resonance energy transfer (FRET), e.g., Light-Cycler™ hybridization probes, where two oligo probes anneal to the amplicon. The oligonucleotides are designed to hybridize in a head-to-tail orientation with the fluorophores separated at a distance that is compatible with efficient energy transfer. Other examples of labeled oligonucleotides that are structured to emit a signal when bound to a nucleic acid or incorporated into an extension product include: Scorpions™ probes (e.g., Whitcombe et al., *Nature Biotechnology* 17:804-807, 1999, and U.S. Pat. No. 6,326,145), Sunrise™ (or Amplifluor™) probes (e.g., Nazarenko et al., *Nuc. Acids Res.* 25:2516-2521, 1997, and U.S. Pat. No. 6,117,635), and probes that form a secondary structure that results in reduced signal without a quencher and that emits increased signal when hybridized to a target (e.g., Lux Probes™).

In other embodiments, intercalating agents that produce a signal when intercalated in double stranded DNA may be used. Exemplary agents include SYBR GREEN™, SYBR GOLD™, and EVAGREEN™. Since these agents are not template-specific, it is assumed that the signal is generated based on template-specific amplification. This can be confirmed by monitoring signal as a function of temperature because melting point of template sequences will generally be much higher than, for example, primer-dimers, etc.

In some embodiments, the quantity of a DNA region is determined by nucleotide sequencing copies in a sample and then determining the relative or absolute number of copies having the same sequence in a sample. Though standard Sanger dideoxy or other nucleotide sequencing methods can be used, sequencing of enriched fragments can be particularly effective when high throughput sequencing is used, e.g., "next generation sequencing methods such as HiSeq™, MiSeq™, or Genome Analyzer (each available from Illumina), SOLiD™ or Ion Torrent™ (each available from Life Technologies) and 454™ sequencing (from Roche Diagnostics). See, e.g., WO 03/004690, WO 03/054142, WO 2004/069849, WO 2004/070005, WO 2004/070007, WO 2005/003375, WO0006770, WO0027521, WO0058507, WO0123610, WO0157248, WO0157249, WO02061127, WO03016565, WO03048387, WO2004018497, WO2004018493, WO2004050915, WO2004076692, WO2005021786, WO2005047301, WO2005065814, WO2005068656, WO2005068089, WO2005078130, and Seo, et al., *Proc. Natl. Acad. Sci. USA* (2004) 101:5488-5493. In some embodiments, sequencing involves single-molecule, real-time (SMRT) sequencing. SMRT sequencing is a process by which single DNA polymerase molecules are observed in real time while they catalyze the incorporation of fluorescently labeled nucleotides complementary to a template nucleic acid strand. Methods of SMRT sequencing are known in the art and were initially described by Flusberg et al., *Nature Methods,* 7:461-465 (2010), which is incorporated herein by reference for all purposes.

In some embodiments, the nucleotide sequence of an amplicon based on target RNA or DNA is determined. Methods of nucleic acid sequencing are well-known in the art. Examples of sequence analysis include, but are not limited to, Maxam-Gilbert sequencing, Sanger sequencing, capillary array DNA sequencing, thermal cycle sequencing (Sears et al., *Biotechniques,* 13:626-633 (1992)), solid-phase sequencing (Zimmerman et al., *Methods Mol. Cell Biol.,* 3:39-42 (1992)), sequencing with mass spectrometry such as matrix-assisted laser desorption/ionization time-of-flight mass spectrometry (MALDI-TOF/MS; Fu et al., *Nature Biotech.,* 16:381-384 (1998)), and sequencing by hybridization (Chee et al., *Science,* 274:610-614 (1996); Drmanac et al., *Science,* 260:1649-1652 (1993); Drmanac et al., *Nature Biotech.,* 16:54-58 (1998)). In some embodiments, the amplicon is sequenced by single-molecule, real-time (SMRT) sequencing. SMRT sequencing is a process by which single DNA polymerase molecules are observed in real time while they catalyze the incorporation of fluorescently labeled nucleotides complementary to a template nucleic acid strand. Methods of SMRT sequencing are known in the art and were initially described by Flusberg et al., *Nature Methods,* 7:461-465 (2010), which is incorporated herein by reference for all purposes.

In some embodiments, nucleotide sequencing does not comprise template-dependent replication of a DNA region. In some embodiments, the amplicon is sequenced by nanopore sequencing. Nanopore sequencing is a process by which a polynucleotide or nucleic acid fragment is passed through a pore (such as a protein pore) under an applied potential while recording modulations of the ionic current passing through the pore. Methods of nanopore sequencing are known in the art; see, e.g., Clarke et al., *Nature Nanotechnology* 4:265-270 (2009), which is incorporated herein by reference for all purposes.

In some embodiments, the amplicon is hybridized to another nucleic acid. In some embodiments, the nucleic acid is linked to a solid support. For example, in some embodiments, the DNA is hybridized to a microarray. A microarray is useful, for example, in monitoring the presence, absence or quantity of multiple sequences in the DNA. In some embodiments, DNA from different samples can be hybridized to one or more nucleic acids, thereby determining the differential amount of one or more particular sequence between the samples, Thus, for example, diseased and healthy cells, or cells obtained at different times, or before and after or during treatment can be compared.

Figure 6:
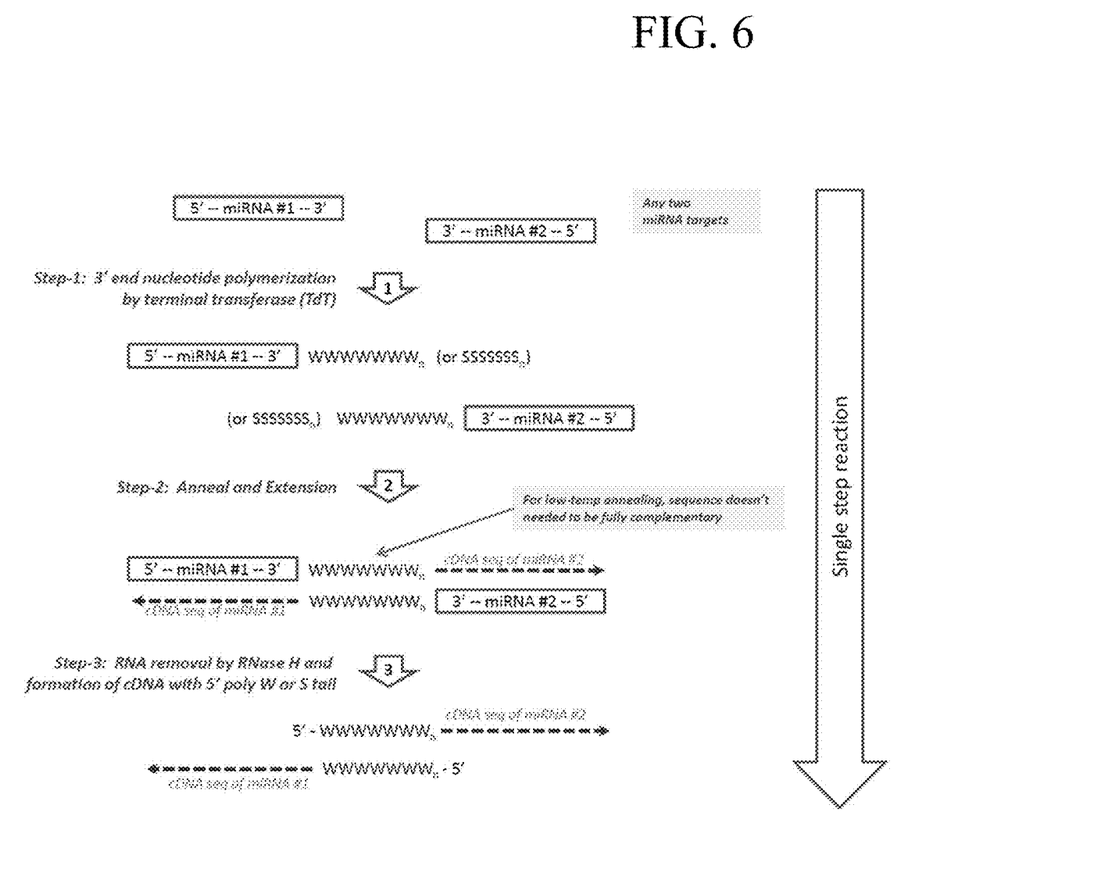
FIG. 6 illustrates steps of a reaction for adding poly-W or poly-S 3' tails to RNAs (e.g., with terminal transferase), annealing the RNAs (e.g., via the poly-W or poly-S sequences), performing a reverse transcription reaction, and eliminating the original target RNA with RNase H activity. The resulting cDNAs can then be detected and analyzed as desired.

A variant of the above RNA detection methods involves using two short target RNAs to act as reverse transcription primers for each other. This aspect is exemplified in FIG. 6. In this embodiment, a mixture comprising at least two RNAs of different sequence is provided. The mixture can have more than two RNAs of different sequence. As the RNAs likely are unrelated in sequence to each other, they will not necessarily anneal to each other in unmodified form. Accordingly, the RNAs in the mixture can be submitted to terminal transferase (TdT) in the presence of nucleotides A/T only or G/C only (template independent nucleotide polymerization). The resulting '3 tailed RNA molecules will have poly-W (A/T) or poly-S(G/C) 3' tails. TdT has lower efficiency to add DNA to the 3' end of RNA molecules and thus, in some embodiments, yeast poly-A polymerase can be used to add several (e.g., ~3 nt) DNA-A sequence to the 3' end of RNA molecule to create an RNA/DNA hybrid with a very short 3' end DNA tail that can act as a substrate for TdT. Due to the random nature and low complexity of the tails, the tails will allow for annealing of some of the 3' tails to other 3' tails, allowing for pairs of RNAs to prime each other. In addition to the terminal transferase, in some embodiments, a polyA polymerase (which catalyzes the template independent addition of AMP from ATP to the 3' end of RNA, see, e.g., Martin and Keller, *RNA* 4:226-230 (1998)), e.g., a yeast poly A polymerase, is included in the terminal transferase reaction. In some embodiments, the temperature of the reaction is initially set such that the poly A polymerase is active and then subsequently the temperature is changed so that the terminal tarnsferase is active. The inclusion of poly A polymerase can provide a few A nucleotides to the RNA, making for a better substrate for terminal transferase. Removal of target RNA sequence can be achieved by inclusion of RNase H or by intrinsic RNase H activity of reverse transcriptase to generate a single-stranded complementary cDNA sequence with a 5' poly-W or G tail. The cDNAs can subsequently be detected as described above, e.g., by PCR, qPCR, or hybridization-based methods like microarray, or sequencing-based methods, including but not limited to RNAseq or next-generation sequencing methods as described above.

In a separate embodiment, a short target RNA can be amplified by an initial reverse transcription step using a short, optionally tailed, primer. The short primer has at least a 3' portion that is complementary to the target RNA 3' end and, optionally also a 5' portion that is not complementary to the target RNA and instead will function as a length extender. This aspect is exemplified in FIG. 5. Reverse transcription with the tailed primer results in a cDNA comprising additional nucleotides complementary to the "tail" of the tailed primer. The tailed primer and a forward primer that anneals to a sequence (ideally at or near the 3' end of) of the cDNA, can subsequently be used to amplify the cDNA.

Figure 5:
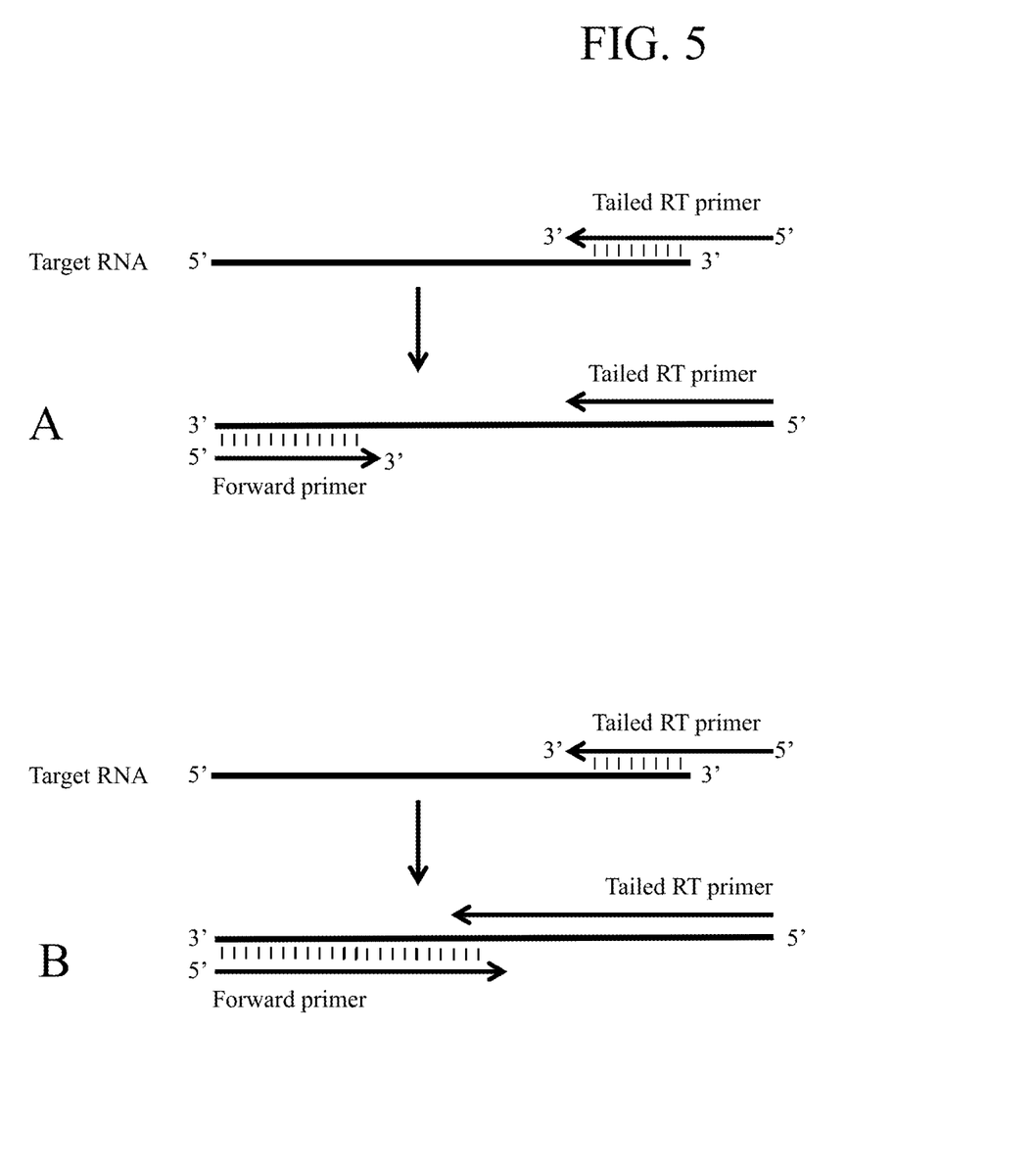

The above-method is of particular use for amplifying very short RNAs, for example RNA having 25 or fewer nucleotides, e.g., 20-25 nucleotides long. RT-PCR is a powerful tool in monitoring mRNA expression level, however, this approach cannot be directly or easily implemented for miRNA and other very short (25 nt or fewer nucleotides) RNA due to its extreme short length (miRNA are typically in the range of 21-25 nt). Typical PCR primers need to be >17 nt to function effectively in PCR reaction that is supported by Taq polymerase, and two primers are required to support exponential amplification. Therefore the length of miRNA (or the corresponding cDNA) is too short to accommodate two standard primers. However, it has been discovered that a polymerase having a small nucleotide footprint (e.g., 6-10 nucleotides long) linked to a DNA binding domain having a small nucleotide footprint (4-6 nucleotides) allows one to use primers as short as 12 or even less (e.g., 10, 11) nucleotides long. As noted above, an exemplary polymerase having a small nucleotide footprint is the Stoffel fragment of Taq polymerase or an analogous fragment from another thermostable (e.g., A family) polymerase and an exemplary DNA binding domain is Sso7d domain. Thus, the primer described above can have, e.g., 6, 7, 8, 9, 10, 11, 12, e.g., 6-12, 6-10, 9-12 contiguous nucleotides complementary to the target RNA and optionally an additional "tail" that is not complementary to the target RNA. In some embodiments, the tail is 4, 5, or 6 (e.g., 4-6) nucleotides, though the tail can be longer or shorter as well. The forward primer can also be designed to have 8, 10, 11, 12, 13, 14, 15 or 16 (e.g., 8-15 or 12-16) or more nucleotides, thereby allowing for the forward and tailed primers to reside on the cDNA or complementary sequence to allow for efficient amplification. Optionally the tailed primer and forward primer will overlap by 1, 2, 3, or more base pairs. See part B of FIG. 5. In some embodiments, the Indeed, a small nucleotide footprint polymerase linked to a small nucleotide footprint DNA binding protein can be further used in an analogous fashion to amplify any short polynucleotides. As an example, formalin or formaldehyde-fixed, paraffin-embedded (FFPE) tissue can contain significantly fragmented polynucleotides (RNA or DNA) that can be a challenged to amplify using standard PCR reagents such as Taq polymerase. Thus, the method described above for amplifying short RNAs can be similarly used for amplifying short (e.g., 20-25 nucleotides) DNA sequences, including but not limited to those in FFPE samples.

Many of the steps (e.g., reverse transcription, amplification, etc.) described above can be performed using routine conditions used in the field of recombinant genetics. Basic texts disclosing the general methods of use in this invention include Sambrook and Russell, Molecular Cloning, A Laboratory Manual (3rd ed. 2001); Kriegler, Gene Transfer and Expression: A Laboratory Manual (1990); and Current Protocols in Molecular Biology (Ausubel et al., eds., 1994-1999).

Samples can be any mixture containing a short RNA. In many embodiments, the sample is derived from a biological fluid, cell or tissue. The sample can be crude or purified. In some cases, the sample is a preparation of RNA from a cell or cells. In some embodiments, the cells are animal cells, including but not limited to, human, or non-human, mammalian cells. Non-human mammalian cells include but are not limited to, primate cells, mouse cells, rat cells, porcine cells, and bovine cells. In some embodiments, the cells are plant or fungal (including but not limited to yeast) cells. Cells can be, for example, cultured primary cells, immortalized culture cells or can be from a biopsy or tissue sample, optionally cultured and stimulated to divide before assayed. Cultured cells can be in suspension or adherent prior to and/or during the permeabilization and/or DNA modification steps. Cells can be from animal tissues, biopsies, etc. For example, the cells can be from a tumor biopsy.

In some embodiments, samples include RNA or DNA targets that only have short amplifiable regions (e.g., wherein a target region has less than 50, 40, 30, 25, or 20 contiguous amplifiable nucleotides), degraded, or are otherwise difficult to amplify due to nucleic acid degradation. For example, formalin-fixed samples can have only short sequences of nucleic acid due to fixation. In other embodiments, ancient nucleic acid samples or samples that have been exposed to chemical or temperature conditions that degrade nucleic acids can be amplified by the methods described herein in view of the method's ability to amplify shorter sequences than typically can be amplified in PCR.

EXAMPLE

Example 1: Model System for Generating miRNA-Specific cDNA Through miRNA-Based Priming A short synthetic RNA molecule of 22 nucleotide long (RNA1, 5' GCAUCAGCGACACACUCAAGAG; SEQ ID NO:1), which mimics the size of naturally existing miRNAs, was annealed to the 3' portion of a longer synthetic RNA (RNA2, 38 nt long, 5' UGAUGACCCCAGGUAACUC-UUGAGUGUGUCGCUGAUGC; SEQ ID NO:2), leaving the 5' portion of RNA2 single stranded. RNA2 (2 nM) and RNA1 (20 pM) were then mixed with reverse transcription reagents (iScript cDNA synthesis kit, SuperScript III, and SuperScript III preblended with RNaseH), and incubated according to the manufaturer's recommendation of the corresponding kits. Subsequently, 2 µl of diluted (25-fold) reverse transcription reaction was added to a qPCR reaction containing 1× DyNamo qPCR mastermix and 250 nM each of PCR primers (PCR1: 5'GCATCAGCGAC; SEQ ID NO:3) and PCR2: 5'CTCTTGAGTGTG; SEQ ID NO:4). The complete mixture was subjected to an amplification protocol that was recommended for DyNamo Mastermix and analyzed on a real-time PCR instrument (CFX384). The results showed that when no RNA substrates were added during the reverse transcription step, only non-specific amplification was observed. When both RNAs were present in the reverse transcription, amplification of the intended target was observed. Moreover, when the reverse transcription enzyme used had high RNaseH activity, either intrinsic to the enzyme (iScript RTase) or through blending (SuperScript III+RNaseH), the Cq value observed was earlier than that obtained with an RTase enzyme having diminished RNaseH activity (SueprScript III). The results support (1) a short RNA strand (e.g. RNA1 in this example) can serve as a primer for the reverse transcription reaction to extend off a long RNA template (e.g. RNA2 in this example) to create an RNA-DNA hybrid, (2) The RNaseH activity of the Reverse Transcriptase cleaves or nicks the RNA (as part of RNA2) involved in RNA-DNA base pairing, which generate additional short RNA primers that can be extended to create cDNA of the original short RNA strand (RNA1), and (3) this cDNA can then be amplified by regular qPCR to allow quantitation of the original input quantity of the short RNA.

Example 2: miRNA Quantitation without Reverse Transcription Primers

Synthetic miR-16 (200 pM) was mixed with (100 ng) purified Hela RNA that contains low amount of low molecular weight RNAs (e.g. miRNA, snoRNA, etc), which was then subjected to reverse transcription using the MMLV RTase in the iScript cDNA synthesis kit, (by Bio-Rad Inc.) and a buffer (a buffer comprising 10% glycerol and 900 µM each of dATP and dTTP, 450 µM each of dGTP and dCTP). As controls, 100 ng of the above Hela RNA and the synthetic miR-16 was also separately (without mixing together) subjected to reverse transcription using the same reagents. Subsequently, 2 µl of diluted (25-fold) reverse transcription reaction was analyzed using SsoAdvanced Universal SYBR Green Supermix (by Bio-Rad, Inc) and primers specific for miR-16 (hsamiR16BF: 5' GGGGTAGCAGCACGTA (SEQ ID NO:5); hsamiR16BR: 5' GGGGCGCCAATATTTAC; SEQ ID NO:6) ( ) and analyzed on real-time PCR instrument (CFX96). The results showed that, when no primers were added during the reverse transcription step, the spiked-in miR-16 was efficiently detected only when it was present in a mixture with Hela RNA (see table below). This result suggested that miR-16 can utilize other RNA molecules as the template and function as a primer to be extended by the reverse transcriptase and generate RNA-DNA fusion. Additional reverse transcription primers can be generated through the cleavage of the RNA strand opposing the DNA region of the RNA-DNA fusion, thus allowing the generation of cDNA for the original miR-16 RNA. The cDNA can then be amplified with miR-16 specific primers, resulting in the detected amplification in qPCR.

TABLE 1

Summary of results

| Experiments | Input synthetic miRNA | Input purified RNA | Detection in qPCR using miR-16-specific primers |
|---|---|---|---|
| 1 | miR-16 | Hela RNA | Cq = 28 |
| 2 | None | Hela RNA | Cq > 35 |
| 3 | miR-16 | none | Cq > 35 |

Example 3: miRNA Amplification Via Semi-Degenerate Priming

Synthetic miR-16 RNA (2-200 pM) was mixed with an enzyme cocktail containing terminal deoxytransferase, yeast polyA polymerase and MMLV reverse transcriptase in the presence of a modified buffer (a buffer comprising 10% glycerol and 900 µM each of dATP and dTTP, 450 µM each of dGTP and dCTP). The mixture was then subjected to incubation at 37 C for 20 min (allowing yeast poly A polymerase to function), 25 C for 15 min (allowing TdT enzyme to function), 37 C for 20 min (allowing RT enzyme to function), and 85 C for 5 min (inactivating all enzymes). Subsequently, 2 µl of the above reaction (diluted by 25-fold) was added to SsoAdvanced Universal SYBR Green Sueprmix in the presence of 250 nM of miR-16-specific primers (same as in example 2) and was amplified and analyzed on a real-time instrument (CFX96). As a positive control, synthetic miR-16 cDNA was amplified in parallel using the same reagent and primers. The results showed that the reactions that contained the synthetic miR-16 RNA or the miR-16 cDNA produced positive amplification signals. Based on the melt curve analysis, the Tm of the amplification products from the miR-16 RNA-based reaction was significantly higher (80 C) than that of the positive control reaction (72 C).

To determine the identity of the amplified products from the miR-16 RNA-based reaction, the products were cloned into a TOPO vector, and 11 clones were sequenced. miR-16 sequence aligned with high identity with sequence contained in each of the 11 clones. The results indicate that when the 3' terminus of miR-16 was extended to contain semi-degenerate sequences using combination of TdT and yeast polyA polymerase, the semi-degenerate region from different extended molecules could anneal to each other and serve as primers in the reverse transcription reaction, thus allowing the cDNA for the miR-16 to be generated and subsequently amplified in qPCR.

Example 4: qPCR Amplification of miRNA cDNA Using Short Primers and Sso-Fusion Polymerase Synthetic miR-16 cDNA (22 nt, 5'TAGCAGCACG-TAAATATTGGCG; SEQ ID NO:7, at 20 pM) was used as the starting template. It was mixed with 250 nM each of two miR16-specific PCR primers, 16 C for (11 nt, 5' TAGCAGCACGT; SEQ ID NO:8) and 16 Crevc (12 nt, 5' CGCCAATATTTA; SEQ ID NO:9), and DyNAmo qPCR supermix, which contained a fusion polymerase of Sso7d domain fused to the polymerase domain of Tbr polymerase. The mixture was subjected to the following amplification protocol: 95 C-15 min, 94 C-10 s, 45×(41 C-20 sec, 60 C-10 s).

The intended target was successfully amplified, resulting in Cq value of 21 and Tm of 62 C for the amplified product. This example demonstrates that very short primers (e.g. 11-12 nt long) can be efficiently utilized by Sso-fusion polymerase to support PCR amplification.

Example 5: Short Primers can be Utilized Sso-Fusion Polymerase More Efficiently in PCR Lambda DNA (2.5 ng per reaction) was used as the template together with PCR primers (150 nM each) in the presence of either wild type Taq polymerase (Taq, 1 unit per reaction) or Sso7d fusion to the Stoffel fragment (Sst, 1 unit per reaction). The primers used were 732R16 (16 nt, 5'TTC-GATATATTCACTC) and 57F12 (12 nt, 5' TTCGT-CATAACT). The final reaction buffer contained 20 mM Tris (pH 8.4), 50 mM KCl, 2 mM MgCl2, and 0.2 mM each dNTPs. The annealing temperature was varied from 46 C to 64 C using gradient and followed by extension at 72 C. The amount of amplified products was determined by adding dsDNA binding dye to the reaction after the amplification was complete and analyzed on a fluorescent plate reader. The intensity of the fluorescent signal correlated to the quantity of the amplified product and the efficiency of the PCR amplification. When the annealing temperature used was between 46 C and 50 C, the amplification product produced by the Sst fusion polymerase resulted in a fluorescence signal of 9000 units, whereas that by the wild type Taq polymerase was below 1000 units. Furthermore, when mismatches were introduced in the first (57F12/1, gTCGT-CATAACT; SEQ ID NO:10) or second residue (57F12/2, TgCGTCATAACT; SEQ ID NO:11) at the 5' terminus of the 12 nt primer, Sst still supported the amplification efficiently and producing similar amount of amplified products as compared to the fully complimentary 12 nt primer. This indicates that primers shorter than 12 nt can be utilized by Sst in PCR amplification.

All documents (for example, patents, patent applications, books, journal articles, or other publications) cited herein are incorporated by reference in their entirety and for all purposes, to the same extent as if each individual document was specifically and individually indicated to be incorporated by reference in its entirety for all purposes. To the extent such documents incorporated by reference contradict the disclosure contained in the specification, the specification is intended to supersede and/or take precedence over any contradictory material.

Many modifications and variations of this invention can be made without departing from its spirit and scope, as will be apparent to those skilled in the art. The specific embodiments described herein are offered by way of example only and are not meant to be limiting in any way.

What is claimed is:

1. A method of generating cDNA from non-polyA tailed RNA, the method comprising adding random poly-W (A/T) or poly-S(G/C) nucleotide sequences to the 3' end of target non-polyA tailed RNA with a terminal transferase to form RNA molecules comprising degenerate nucleotide sequences at the 3' end of the molecules;

submitting the RNA molecules comprising the random poly-W or poly-S nucleotide sequences to conditions such that the RNA molecules comprising the random poly-W or poly-S nucleotide sequences anneal to form a duplex of a first and second RNA molecule annealed to each other via the random poly-W or poly-S nucleotide sequences; and extending the 3' ends of the molecules in the duplex with a DNA polymerase such that the 3' ends act as a primer to form (i) a first cDNA complementary to the first RNA molecule of the duplex and (ii) a second cDNA complementary to the second RNA molecule of the duplex, wherein the first and second cDNAs further comprise a 5' sequence that is a complement of the random poly-W or poly-S nucleotide sequence.

2. The method of claim 1, wherein the RNA is a miRNA, snoRNA, piRNA, or lncRNA.

3. The method of claim 1, further comprising digesting the RNA molecules with an RNAse H activity.

4. The method of claim 1, further comprising amplifying the first or second cDNA with a primer that anneals to the complement of the degenerate sequence.

5. The method of claim 1, wherein the adding further comprises contacting the non-polyA tailed RNA with a poly A polymerase.

6. The method of claim 4, wherein the amplifying comprises generating an amplicon, and the method further comprises nucleotide sequencing the amplicon.

7. The method of claim 1, further comprising quantifying the amount of the non-tailed RNA in the sample.

* * * * *

SEQUENCE LISTING

```
<160> NUMBER OF SEQ ID NOS: 11

<210> SEQ ID NO 1
<211> LENGTH: 22
<212> TYPE: RNA
<213> ORGANISM: Artificial Sequence
<220> FEATURE:
<223> OTHER INFORMATION: synthetic RNA oligonucleotide

<400> SEQUENCE: 1
gcaucagcga cacacucaag ag                                              22

<210> SEQ ID NO 2
<211> LENGTH: 38
<212> TYPE: RNA
<213> ORGANISM: Artificial Sequence
<220> FEATURE:
<223> OTHER INFORMATION: synthetic RNA oligonucleotide

<400> SEQUENCE: 2
ugaugacccc agguaacucu ugaguguguc gcugaugc                             38

<210> SEQ ID NO 3
<211> LENGTH: 11
<212> TYPE: DNA
<213> ORGANISM: Artificial Sequence
<220> FEATURE:
<223> OTHER INFORMATION: synthetic primer

<400> SEQUENCE: 3
gcatcagcga c                                                          11

<210> SEQ ID NO 4
<211> LENGTH: 12
<212> TYPE: DNA
<213> ORGANISM: Artificial Sequence
<220> FEATURE:
<223> OTHER INFORMATION: synthetic primer
```

-continued

```
<400> SEQUENCE: 4
ctcttgagtg tg                                                         12

<210> SEQ ID NO 5
<211> LENGTH: 16
<212> TYPE: DNA
<213> ORGANISM: Artificial Sequence
<220> FEATURE:
<223> OTHER INFORMATION: synthetic primer

<400> SEQUENCE: 5
ggggtagcag cacgta                                                     16

<210> SEQ ID NO 6
<211> LENGTH: 17
<212> TYPE: DNA
<213> ORGANISM: Artificial Sequence
<220> FEATURE:
<223> OTHER INFORMATION: synthetic primer

<400> SEQUENCE: 6
ggggcgccaa tatttac                                                    17

<210> SEQ ID NO 7
<211> LENGTH: 22
<212> TYPE: DNA
<213> ORGANISM: Artificial Sequence
<220> FEATURE:
<223> OTHER INFORMATION: synthetic primer

<400> SEQUENCE: 7
tagcagcacg taaatattgg cg                                              22

<210> SEQ ID NO 8
<211> LENGTH: 11
<212> TYPE: DNA
<213> ORGANISM: Artificial Sequence
<220> FEATURE:
<223> OTHER INFORMATION: synthetic primer

<400> SEQUENCE: 8
tagcagcacg t                                                          11

<210> SEQ ID NO 9
<211> LENGTH: 12
<212> TYPE: DNA
<213> ORGANISM: Artificial Sequence
<220> FEATURE:
<223> OTHER INFORMATION: synthetic primer

<400> SEQUENCE: 9
cgccaatatt ta                                                         12

<210> SEQ ID NO 10
<211> LENGTH: 12
<212> TYPE: DNA
<213> ORGANISM: Artificial Sequence
<220> FEATURE:
<223> OTHER INFORMATION: synthetic oligonucleotide

<400> SEQUENCE: 10
gtcgtcataa ct                                                         12

<210> SEQ ID NO 11
<211> LENGTH: 12
```

-continued

```
<212> TYPE: DNA
<213> ORGANISM: Artificial Sequence
<220> FEATURE:
<223> OTHER INFORMATION: synthetic oligonucleotide

<400> SEQUENCE: 11
tgcgtcataa ct                                                          12
```